United States Patent [19]

Guirguis

[11] Patent Number: 5,022,411
[45] Date of Patent: Jun. 11, 1991

[54] MODULAR FLUID TESTING DEVICE

[75] Inventor: Raouf A. Guirguis, Rockville, Md.

[73] Assignee: La Mina Ltd., British Virgin Isls.

[21] Appl. No.: 440,117

[22] Filed: Nov. 22, 1989

Related U.S. Application Data

[63] Continuation-in-part of Ser. No. 408,547, Sep. 18, 1989.

[51] Int. Cl.⁵ .............................................. A61B 5/00
[52] U.S. Cl. ..................................... 128/771; 604/317
[58] Field of Search ............... 128/760, 762, 771, 761; 604/317, 318

[56] References Cited

U.S. PATENT DOCUMENTS

| | | | |
|---|---|---|---|
| 3,312,221 | 4/1967 | Overwent | 604/317 |
| 4,473,530 | 9/1984 | Villa-Real | 128/762 |
| 4,492,258 | 1/1985 | Lichtenstein et al. | 128/761 |
| 4,661,100 | 4/1987 | Rechsteiner | 604/317 |
| 4,685,472 | 8/1987 | Muto | 128/760 |

FOREIGN PATENT DOCUMENTS

PCT/US89/-
02914  1/1990  PCT Int'l Appl. .

*Primary Examiner*—Max Hindenburg
*Attorney, Agent, or Firm*—Gipple & Hale

[57] ABSTRACT

An apparatus for testing biological molecular indicators in urine comprising a tubular container with a plunger assembly and associated testing assembly. Urine is collected in the tubular container mixed with labelled antibodies and is caused by the plunger assembly to flow against a testing surface provided with immobilized antibodies which capture antigens complexed with labelled antibodies. The enzymes of the labelled antibodies are colored by a reactant solution to indicate the presence or absence of specific antigens in the tested urine.

24 Claims, 7 Drawing Sheets

MODULAR FLUID TESTING DEVICE

RELATED CASES

This is a continuation-in-part application of U.S. Pat. application Ser. No. 07/408,547 filed Sept. 18, 1989, pending.

BACKGROUND OF THE INVENTION

The present invention is directed to medical and laboratory specimen collecting and testing equipment, and more specifically to an apparatus for collecting and concentrating biological markers containing fluids and testing such biological fluids.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging collects and holds different fluid components which will negate the test results or result in false data being obtained when the specimen is tested.

One of the problems in collecting biological fluid specimens occurs not only during the collection of the specimens but also in the transport or shipment of the specimens after collection to the laboratory for analysis.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial which in connection with the cap allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

One such specimen collection device shown by U.S. Pat. No. 4,040,791 discloses a collection receptacle having a nipple upon which is mounted a specimen container which receives a predetermined amount of the specimen in a sealed condition. The specimen container is provided with an integally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle apparatus which obtains fluid samples such as urine with a minimum chance for spillage and contamination between collection and testing as well as a need to separate various biological components of the urine. In using the present invention testing can be performed quickly and accurately with minimum time.

For some testing, particularly where antigens are being removed from the body fluids for a variety of tests it is desirable to remove the antigens from the urine fluid so that various test procedures can be run. It is also desirable to do so with minimal exposure of laboratory personnel to the sample subject of testing. Previously this has been accomplished by a series of tests involving a number of different containers and expensive laboratory equipment. Mass testing using such a series of tests is expensive, time consuming, and often unsatisfactory.

BRIEF SUMMARY OF THE INVENTION

There is provided in the practice of the invention according to the presently preferred embodiment, a urine collection and testing device. This device is in the form of a tubular device having a transportable testing assembly with a coloration membrane holding immobilized antibodies selected to capture specific antigens contained in the urine which are markers for various kinds of cancers.

In the accompanying drawings, there is shown an illustrative embodiment of the invention from which these and other objectives, novel features and advantages will be readily apparent.

DETAILED DESCRIPTION OF THE INVENTION

The preferred embodiment and best mode of the invention is seen in FIGS. 1 through 12. The invention shown therein comprises a modular separable fluid testing device. While the invention can be used for any body fluid such as sputum, blood, body fluids or urine, it is primarily designed for use in collecting urine/blood samples for use in testing for the presence of various kinds of cancer in the body.

As shown in FIGS. 1-4, a sample testing apparatus 20 is constructed of polystyrene and comprises a tubular collection container 22, a cap member 30 and a plunger unit 50 with associated test assembly 70.

Figure 1:
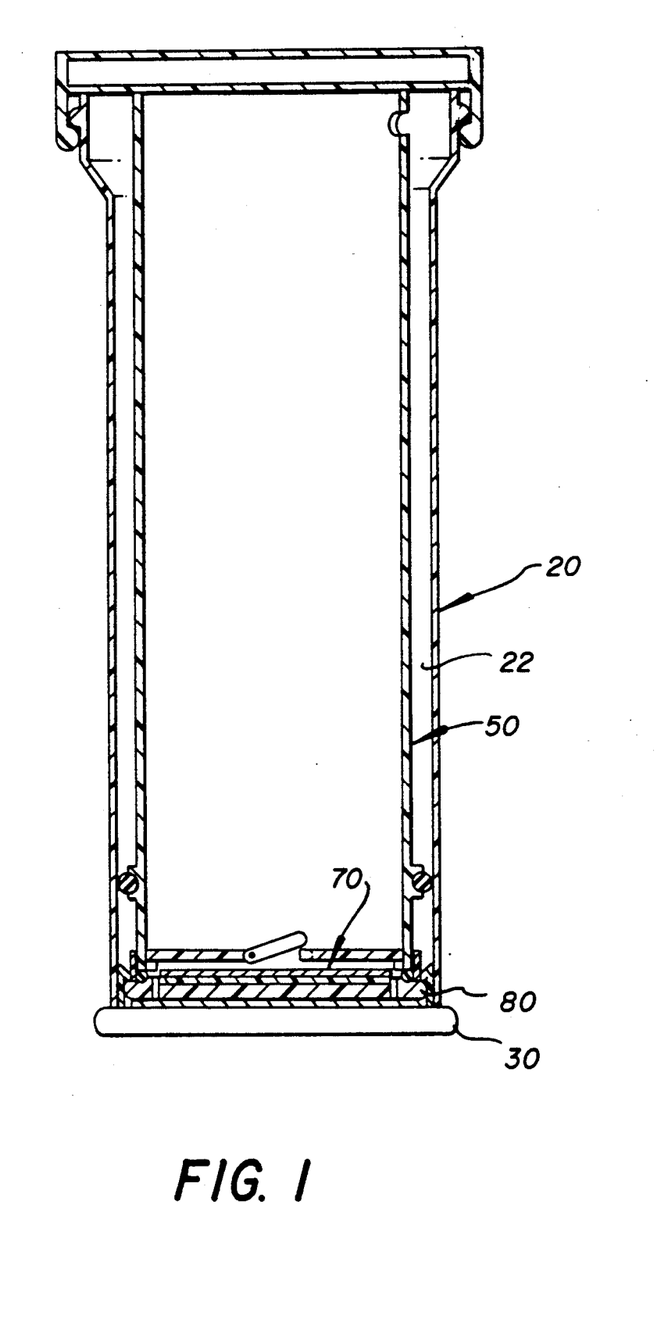
FIG. 1 is a cross sectional view of the assembled inventive testing apparatus.
Figure 2:
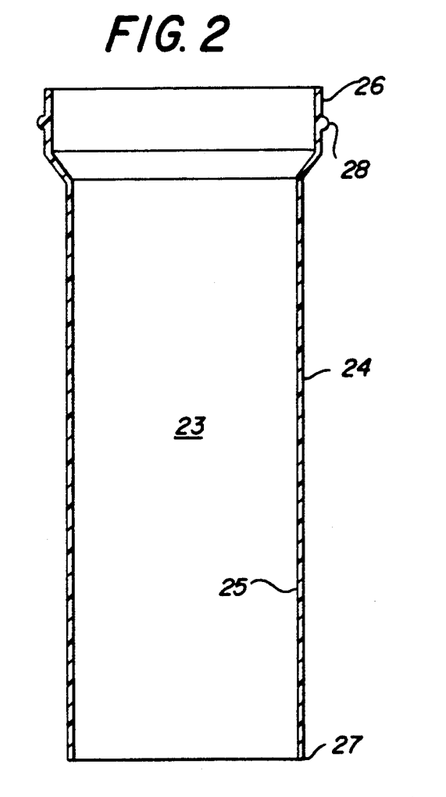
FIG. 2 is a cross sectional view of the fluid collection container of the testing apparatus of FIG. 1.
Figure 3:
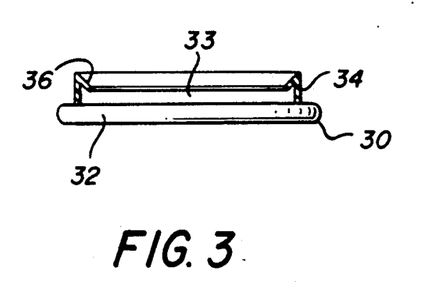
FIG. 3 is a cross sectional view of the cap for the fluid collection container of FIG. 2.
Figure 4:
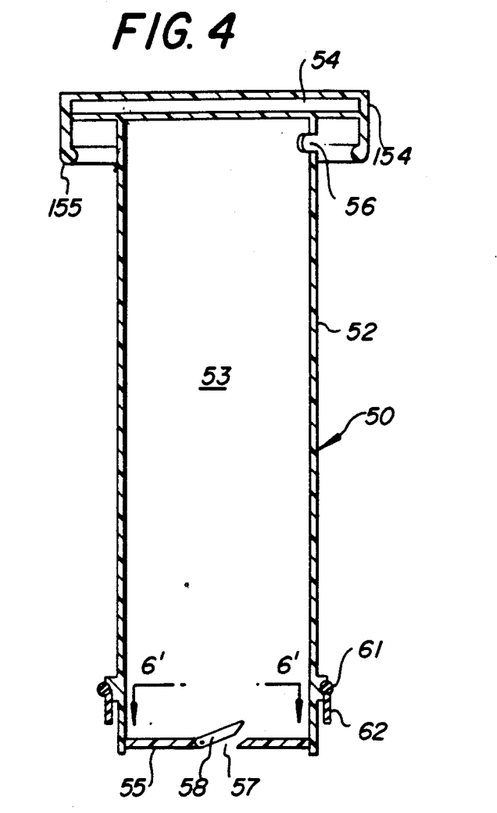
FIG. 4 is a cross sectional view of the plunger assembly of the testing apparatus of FIG. 1.

The tubular collection container 22 as shown in FIG. 2 is constructed with a tubular open ended cylindrical body 24 defining a chamber 23 with an open flared end portion 26 formed on one end with a circular rib 28. The flared end portion 26 has a wide mouth to more easily receive body fluid such as urine which is loaded into the unit. A cap member 30 is removably secured to the other end 27 of the collection unit 22 by virtue of a friction fit over the body 24. The cap member 30 comprises a disc shaped body 32 with an upwardly extending flexible skirt member 34. A downwardly extending flange 36 extends inward from the skirt member S4 to hold the test assembly 70 in place once it is carried by the plunger past end 27 of container 22 and flange 36.

The plunger unit 50 as shown in FIGS. 1, 4, 6 and 10 is designed to fit within cylindrical body 24 of the collection unit 22 and slideably move along the interior wall surface 25 in a sealed relationship holding a test assembly 70. The plunger assembly 50 is constructed of a transparent plastic comprising a hollow cylindrical plunger body 52 provided with a thumb cover 54 and a bottom end wall 55. The cover 54 has a downwardly extending skirt 154 with a ribbed lip 155 which snap fits over the circular rib 28 on the flared end 26 to hold the plunger assembly in a fixed relationship to the container body 24. An air release aperture 56 is formed in the plunger body 52 so that there is communication between the interior chamber 53 of the plunger body into the outside atmosphere. The bottom endwall 55 is provided with a circular throughgoing aperture 57 which communicates with the chamber 53 and the membrane surface 72. A one-way flap valve 58 is seated over the aperture 57 and is hingedly mounted to the bottom end wall at 59 as is clearly shown in FIGS. 6 and 8. If desired, the flap member 58 can be seated in a valve seat (not shown) which is cut into the surface of the bottom end wall surface so that it is seated flush with the bottom wall surface. Mounted around the plunger body in an annular channel cut into the exterior surface of the body 52 is an O-ring 61 with downwardly extending gasket number 62. This O-ring slideably engages and forms a fluid seal against the interior surface 25 of collection unit 22 while the gasket member 62 seats against the outer surface of skirt 86.

Figures 7, 7B:
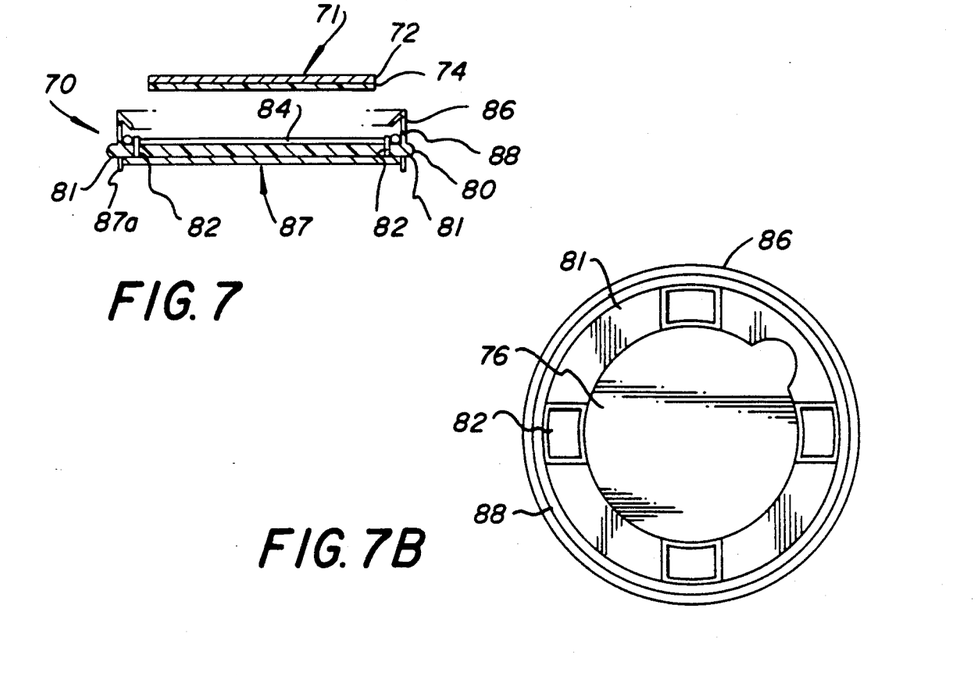
FIG. 7 is an exploded enlarged cross sectional view of the test assembly with associated top plan views of the test assembly shown as indicated in FIG. 7A and 7B.
Figure 7A:
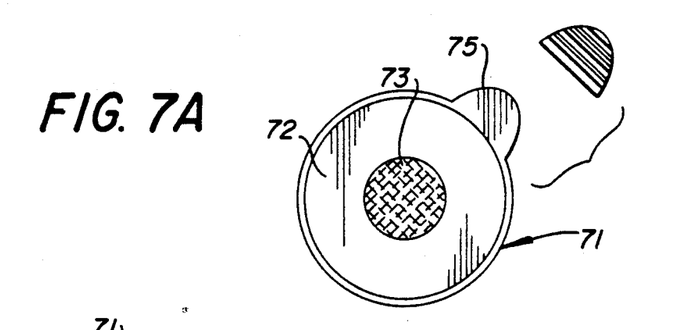
Figure 8:
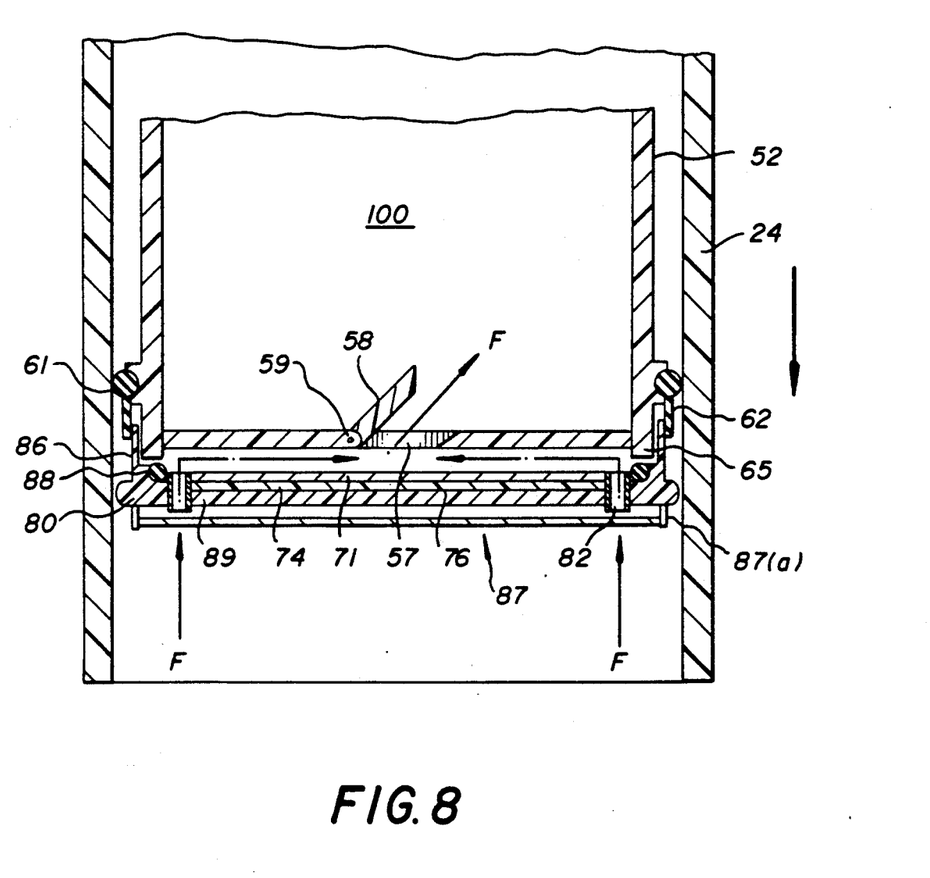
FIG. 8 is an enlarged cross sectional view of the test assembly with direction of movement of the plunger shown by arrow P and direction of flow of the fluid shown by arrows F.
Figure 9:
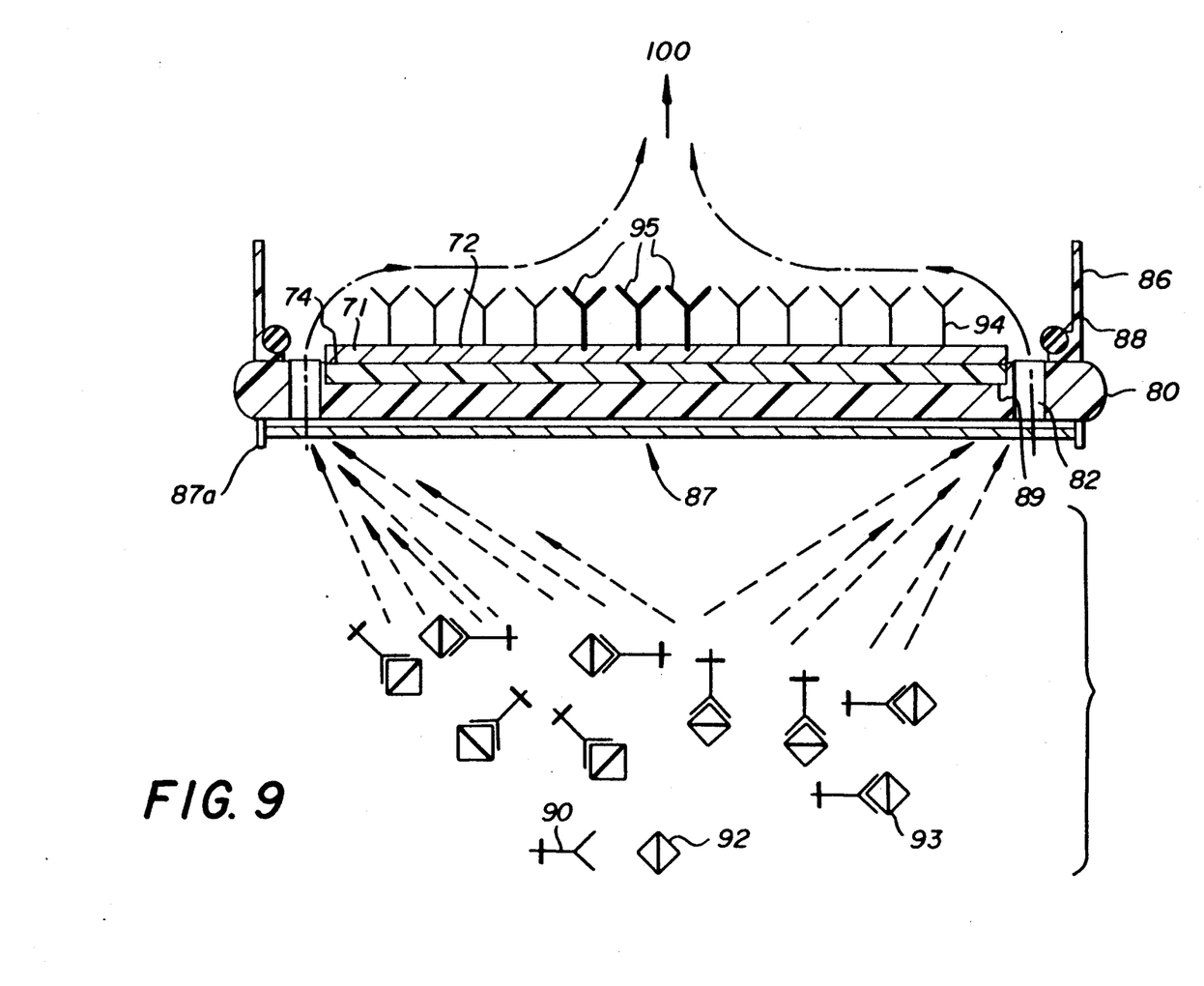
FIG. 9 is an enlarged cross sectional schematic showing flow of fluid with antigen, labelled antibodies and complexed antibodies through the testing assembly and mounting of the immobilized antibodies on a surface matrix.
Figure 10:
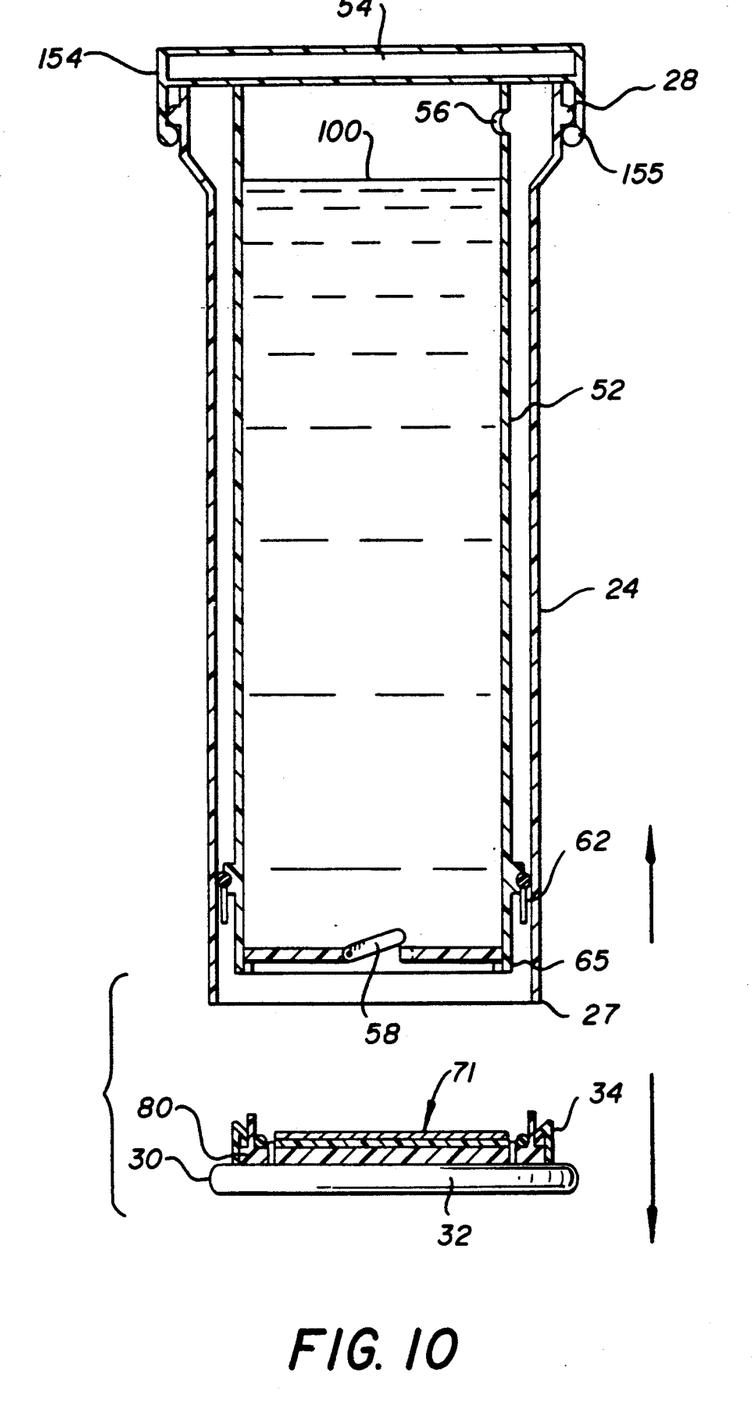
FIG. 10 is a cross sectional view of the inventive testing apparatus with the testing assembly removed.

The test assembly 70 as shown in FIGS. 7 and 8 is constructed with a cylindrical base member 80 provided with a plurality of pass through ports or openings 82 and defines a membrane disk seat 84. A cylindrical skirt 86 is integrally formed on the base member 80 which has a diameter substantially the same as rim 65 in order to provide a tight friction fit for attachment of the test assembly to the rim. An "O" ring 88 rests on top surface 81 of base member 80 abutting the inner surface of the skirt 86 to provide a fluid tight seal between the skirt 86 and rim 65. A test disc 71 comprising a solid plastic base member 74 with a handle tab 75 and a membrane member 72 provided with immobilized ligand is seated on the base member 80 inside the ports 82. The circular membrane 72 is glued to the base member 74 or takes the form of a coating. The captured antibodies are immobilized on the matrix 72 by a procedure known as solid phase immobilization of the antibodies. The tab handle 75 allows the disc 71 to be picked up from the seat B4 without destroying any of the test antigens captured on the disc. This allows the disc to then be inserted into a reflectometer (color reader) for accurate quantification of the test result. It is also envisioned that the test handle can be marked with marking indicia such as bar codes to aid in identifying patients when large numbers of specimens are being tested.

It should be noted that the air contained in chamber 53 is pushed out by the fluid entering through valve 58 into chamber 53, through air release aperture 56 into a chamber formed by the concentric outer surface of the plunger body 52 and the inner surface 25 of sample collection unit 22. The test assembly 70 is pushed down by the rim 65 of the plunger body until it enters into the cap cavity 33 of cap member 30 past the flange 36. When the testing assembly 70 is seated in the cap member 30, the fluid entering the body chamber 53 through valve 58 will be trapped inside it even after removal of the cap member 30 and testing assembly 70 since the valve is single directional and will prevent fluid from flowing out of the chamber 53.

Figure 11:
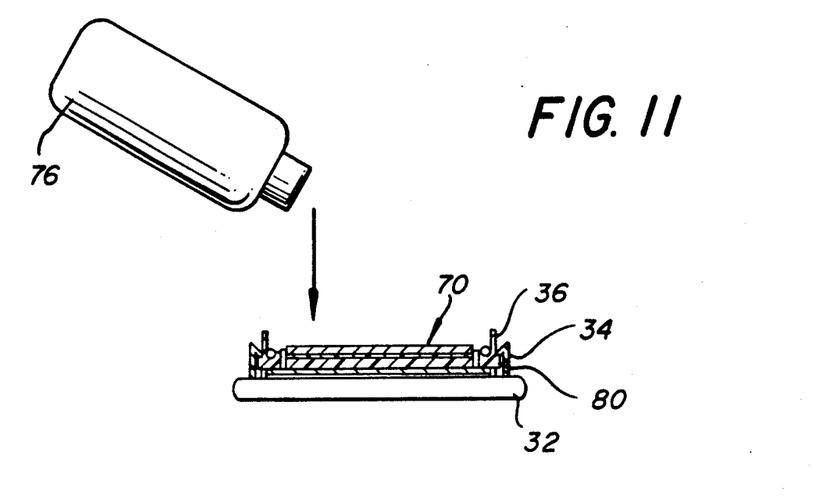
FIG. 11 is a view of the testing assembly showing color developing solution being added to the testing membrane.

The membrane surface or matrix 72 is provided with immobilized antibodies 94 which, through flow contact with the fluid 100, captures the specific component of the fluid which is to be tested; in this example, specific antigens caused by cancer cells. The cap member 30 is then pulled off of the tubular collection container end 27 with the test assembly 70 contained therein (held by flange 36), the plunger assembly 50 remaining with the tubular collection container 24, and membrane or matrix 72 is tested with a color developing solution 76 as seen in FIG. 11. It is within the scope of the invention that disc 71 can be removed separate as so desired for shipment or testing.

Chamber 23 of the collection container contains lyophilized primary labelled antibodies 90 in biological fluid 100 (urine) having a binding site contoured to the epitope structure and chemistry of antigen 92. This antigen has been previously determined as being a marker for a specific type of cancer. The antibodies 90 are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme. Membrane or surface 72 mounted on base member 74 contains antibodies 94 immobilized (covalently bound) thereto for reception of the complexed antibodies 93 and is provided with an area 73 holding antibodies 95 which act as a control. The antigen 92 has epitopes which have a high affinity for the binding sites of the primary labelled antibody 90 and immobilized antibody 94. The principle of affinity chromatography requires that a successful separation of a biospecific ligand is available and that it can be chemically immobilized to a chromatographic bed material, the matrix (surface 72). Numbers of methods well known in the art have been used to couple or immobilize the antibodies to a variety of matrixes. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by Bio-Probe International, and Actigel-ALD manufactured by Sterogene Bioseparation Inc.)

Another advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10-100 cm/min).

After the urine has passed over the membrane 72 and deposited complexed antibodies 93 on the immobilized antibodies 94, the membrane or surface matrix 72 is preferably soaked with ABTS solution 76. A hydrogen peroxide ($H_2O_2$) solution may be alternately placed on the membrane when OPD or TMB or other dual substrate systems are used.

The color solution 76 used on the membrane or matrix 72 is preferably a substrate manufactured by Kirkegaard & Perry Labs under one of several acronyms namely: ABTS (2,2'-azino-di-[3-ethylbenzthiazoline sulfonate (6)]; OPD (ortho-phenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbance over the cut-off of the reader, the faster substrate may in fact reduce the signal-to-noise ratio.

The preferred color solution 76 as shown in FIG. 11 of the present invention is ABTS. The preferred ABTS substrate is a one-component substrate. The HRP label on the primary antibody 90 is turned by the ABTS to a blue-green color and there is no change in color or absorbance when the reaction is stopped with SDS (sodium dodecyl sulfate). If the assay optimization indicates the sensitivity of the immunoassay is limited by the color generated by the HRP substrate then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

Figures 12A, 12B:
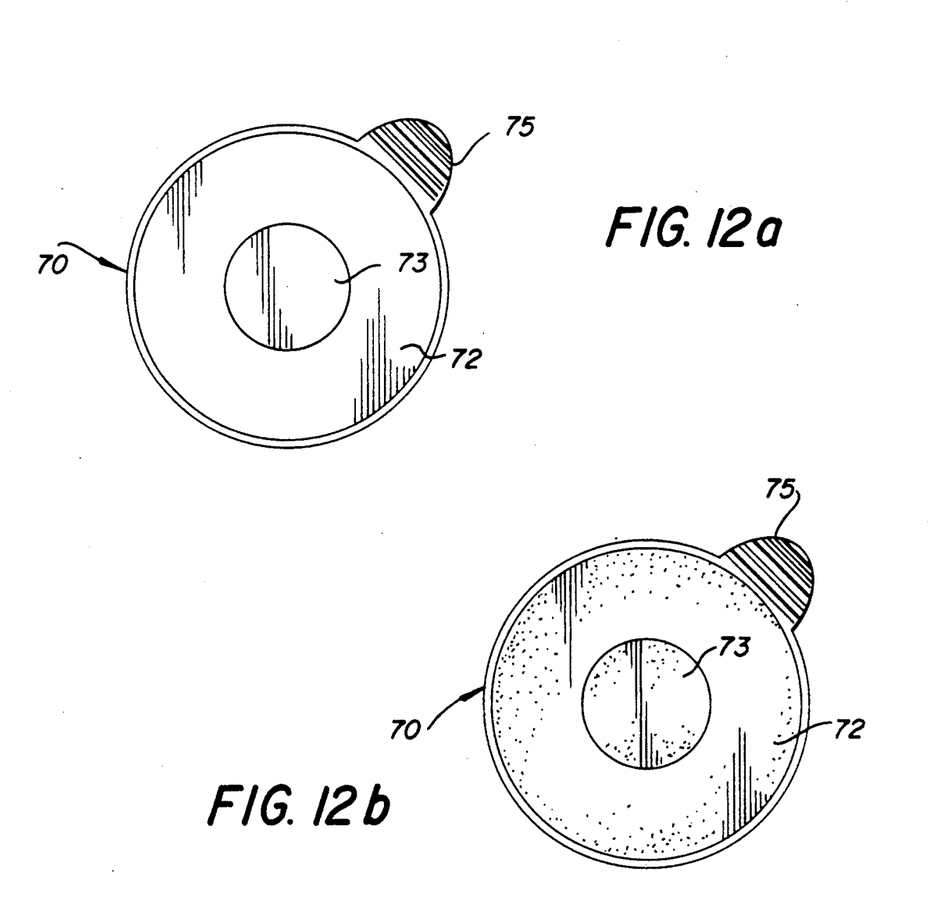
FIG. 12(A) is a top plan view of the testing disc shown in FIG. 11 showing negative test results.
FIG. 12(B) is a top plan view of the testing disc shown in FIG. 11 showing positive test results.

The membrane material 72 with matrix and immobilized ligand (in this case immobilized antibody 94 an control antibody 95) having had flow contact with the urine fluid, captures through antigen-antibody reaction or immune reaction the specific ligand component carried by the fluid namely, the complexed primary labelled antibody 90 and antigen 92 which was formerly contained in fluid 100. This antibody 90 as previously noted was provided prelabelled with coloring enzyme HRP. When the specific antigen 92 is present in the fluid testing sample 100 which is added to the container, the antigen 92 reacts with the antibody 90 to form antigen-antibody complexes 93. The complexed antigen-antibody 93 carried by the fluid passes through ports or apertures 82 in the disc body 80 over the membrane surface 72 so that antigens 92 are captured by immobilized antibodies 94. This labelling enzyme of the antibody 90 reacts with the ABTS poured on the membrane surface 72 turning the surface of the membrane into a blue green color as is clearly shown in FIG. 12 POSITIVE. If there is an absence of the antigen 92 in the specimen sample 100 the antibody 90 will remain unoccupied and will not bind to the immobilized antibodies 94 as is shown in FIG. 12 NEGATIVE. On the other hand, if the antigen 92 is present, antigen-antibody complexes 93 will be formed and held on the membrane surface for reaction with the ABTS solution 76. The degree of color developed should correlate with the amount of prelabelled antibody/antigen complexes 93 which in turn correlates with the amount of antigen 92 present in the sample 100. The positive control area 73 with immobilized antibodies 95 reflects the current state of the coloring reagents as well as the prelabelled antibody at the time the test is performed.

Under normal conditions, urine contains a small number of cells and other particulate matters shed from the entire length of the urinary tract. These elements are usually known as urinary sediments. Examination of urinary sedimentation is a routine procedure in urine analysis. With disease, these cells as well as other formed elements are increased and may help to localize the site and type of injury. For example, excessive numbers of RBCs many indicate infection, tumor, stones or inflammation. Excessive numbers of leukocytes may indicate infection or other inflammatory disease. In contrast to the hypocellular nature of normal urine, neoplastic cells (e.g., transitional, squamous and columnar cells) are shed more frequently in malignant conditions of the bladder epithelium.

Particulate elements in urine can be separated by methods well known in the art, e.g., centrifugatation of 10 to 15 ml of freshly voided urine for five minutes at a slow speed (1500 rpm). The urinary sediments are then fixed and stained with a wide range of urinary sediment stains (e.g., Benzidine or orthotolidine stain used to identify hemoglobin, Gram stain used to differentiate between gram positive and gram negative bacteria, Papanicolaou stain useful in identifying malignant cells). By forcing urine through a membrane filter with holes large enough to allow the urine to go through and small enough to prevent the cells from passing; the residue on the filter can be fixed and stained for proper microscopic visualization. Fifty percent alcohol solution is the most commonly used fixative to preserve the cells for long periods until properly stained for microscopic examination.

Figure 5:
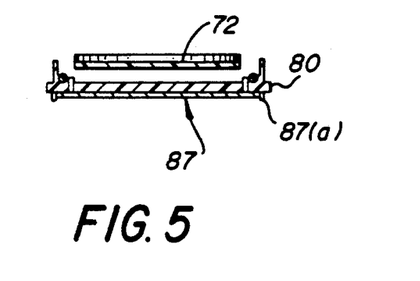
FIG. 5 is a cross sectional view of the test assembly of the testing apparatus of FIG. 1.
Figure 6:
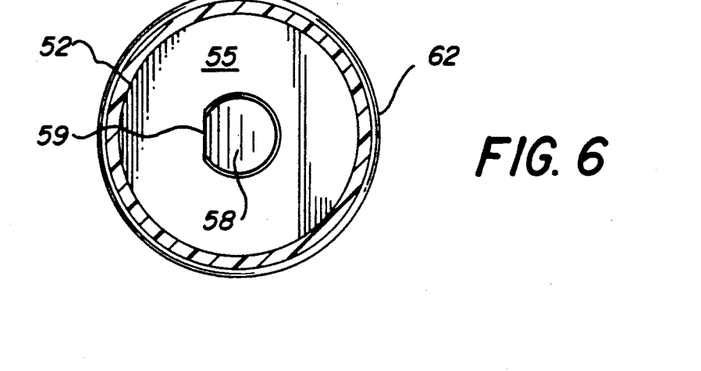
FIG. 6 is a top plan view of the bottom wall of the plunger assembly taken along line 6'—6' of FIG. 4.

In the present invention, an optional prefilteration membrane member 87 as shown in FIG. 5, e.g., nuclepore polycarbonate membranes with diameter pore sizes of 2 to 5 microns can be affixed on the underside of the base member 80 on skirt support 87(a). At the end of the test, the test assembly 70 is removed for color development and measurement of test results. If the test result is positive, a few drops of the fixative solution are then added to the base member 80 to fix the cells trapped under the prefilteration membrane 87. The base member 80 is then sealed with an optional cap (not shown) and shipped to the laboratory for complete urine cytology. This will provide a more thorough analysis of the patient's urine since urine cytology is the most widely accepted method in diagnosing urinary tract cancers.

It can thus be seen that the present invention provides a unique modular usage for collecting, concentrating, and testing the biological fluid sample.

In the foregoing description, the invention has been described with reference to a particular preferred embodiment, although it is to be understood that specific details shown are merely illustrative, and the invention may be carried out in other ways without departing from the true spirit and scope of the following claims:

The embodiments of the invention in which an exclusive property or privilege is claimed are defined as follows:

1. An apparatus for testing biological fluid for the presence of specific antigens comprising a tubular container adapted to receive a biological fluid, piston means slidably mounted in said tubular container, said piston means including valve means allowing fluid to flow therethrough, a testing assembly removably mounted to and transported by said piston means, said testing assembly comprising a base member support means, and immobilized ligand means mounted on said base member.

2. An apparatus as claimed in claim 1 wherein said piston means comprises a housing defining aperture means and said valve means is a one way flap valve seated over said aperture means.

3. An apparatus as claimed in claim 1 wherein said immobilized ligand means comprises a disc member, said disc member including a surface with immobilized ligands thereon.

4. An apparatus as claimed in claim 3 wherein said immobilized ligands are specific immobilized antibodies selected to capture specific antigens.

5. An apparatus as claimed in claim 3 wherein said disc member surface includes a control surface and handle means.

6. An apparatus as claimed in claim 1 wherein said base member support means comprises a support member, port means defined in said support member to allow fluid flow therein, and skirt means extending from said support member to engage said piston means and hold said testing assembly on said piston means.

7. An apparatus as claimed in claim 4 including a prefilteration membrane means mounted to said support member and covering said port means.

8. An apparatus as claimed in claim 1 wherein said testing assembly includes an "O" ring means mounted to said piston means, said "O" ring means comprising an "O" ring and gasket means extending from said "O" ring.

9. An apparatus as claimed in claim 1 wherein said tubular container includes cap means removably secured to said housing.

10. An apparatus as claimed in claim 9 wherein said cap means comprise a cap body, a skirt extending from said cap body which is adapted to frictionally fit on said tubular container, and flange means extending from said skirt, said flange means being adapted to engage said test assembly and flex allowing said test assembly to be held in said cap means.

11. An apparatus for collecting molecular specimens from biological fluids and marking said specimens with a color indicator for visual identification comprising a container; biological fluid with labelled antibodies specifically selected to capture specific antigens contained in said container, means to transport a testing unit in said container and provide fluid communication of said testing unit with said biological fluid, said testing unit comprising a disc means with immobilized antibody means having receptors which capture the labelled antibodies in said biological fluid and colorization means adapted to react with said labelled antibody means to create a visual color indicator a surface of said disc means indicating the presence of said specific antigens.

12. An apparatus as claimed in claim 11 wherein said colorization means is ABTS and said labelled antibodies are labeled with HPR.

13. An apparatus as claimed in claim 11 wherein said means to transport a testing unit is a transporter assembly slidably mOunted in said container.

14. An apparatus as claimed in claim 13 wherein said transporter assembly is provided with valve means allowing fluid flow therethrough.

15. An apparatus for testing biological fluids such as urine for the presence of specific antigens comprising; a container adapted to hold urine, plunger means slidably mounted in said container, a testing assembly removably mounted to and carried by said plunger means, said testing assembly comprising a support assembly and immobilized ligand means mounted to said support assembly, said immobilized ligand means being adapted to capture specific predesignated antigens from urine, fluid flow means formed on said plunger means allowing urine to flow from said fluid container into said plunger means and engage said immobilized ligand means said fluid flow means comprising valve means.

16. An apparatus as claimed in claim 15 wherein said valve means is a one way flap valve.

17. An apparatus as claimed in claim 15 wherein said immobilized ligand means comprises a base member, a matrix surface on said base member and immobilized antibodies on said matrix surface.

18. An apparatus as claimed in claim 17 wherein said base member includes handle means.

19. An apparatus as claimed in claim 17 wherein said base member is provided with identifying marking indicia.

20. An apparatus as claimed in claim 15 wherein said testing assembly comprises a support member, skirt means connected to said support member, flange means extending inwardly from said skirt member and port means defined by said support member allowing fluid to flow therethrough.

21. An apparatus as claimed in claim 17 including a second area on said matrix surface which acts as a control area.

22. An apparatus for testing biological fluids such as urine for the presence of specific antigens comprising; a container adapted to hold urine, plunger means slidably mounted in said container, a testing assembly removably mounted to and carried by said plunger means, said testing assembly comprising a support member, skirt means connected to said support member, a base member holding means extending from said skirt means and port means defined by said support member allowing fluid to flow therethrough to immobilized ligand means removably mounted to said support member, said immobilized ligand means comprising a base member, a ligand matrix surface on said base member and immobilized antibodies on said matrix surface selected from specific antibodies adapted to capture specific predesignated antigens from urine, fluid flow means formed on said plunger means allowing urine to flow from said fluid container into said plunger means and engage said immobilized ligand means so that antigens contained in the urine, are captured and held by the immobilized antibodies on said matrix surface.

23. A method of testing for predetermined molecular bodies in a urine specimen comprising the steps of:
   a. collecting urine into an apparatus for collecting biological fluids comprising an elongated tubular collector container;
   b. treating urine with a buffer solution containing prelabelled antibodies;
   c. passing the urine through a treatment container comprising a cylindrical hollow plunger carrying an immobilized removable antibody means by transporting the treatment container through the urine collector container to capture antigens in the urine;
   d. removing the immobilized removable antibody means with captured antigen from the urine collector container; and
   e. contacting color developing solution with the removable antibody means with captured antigen to obtain a visual color test result which indicates the presence or absence of specific marker antigens.

24. A method of testing for predetermined molecular bodies in a urine specimen as claimed in claim 23 including after step b. the step of forcing urine through a membrane filter to allow the urine to go through while preventing cells and other biological sediments from passing through the membrane trapping said cells and biological sediments on the membrane filter.

* * * * *